United States Patent [19]

Brown

[11] Patent Number: 4,484,914
[45] Date of Patent: Nov. 27, 1984

[54] INTRAVENOUS CATHETER RESTRAINT

[76] Inventor: Curtis W. Brown, 387 Chevy Chase Dr., Reno, Nev. 89509

[21] Appl. No.: 415,049

[22] Filed: Sep. 7, 1982

[51] Int. Cl.$^3$ ............................................. A61M 25/02
[52] U.S. Cl. .............................. 604/180; 128/DIG. 26
[58] Field of Search ....................... 128/133, DIG. 26; 604/174–180

[56] References Cited

U.S. PATENT DOCUMENTS

| | | | |
|---|---|---|---|
| 3,677,250 | 7/1972 | Thomas | 604/180 |
| 3,834,380 | 9/1974 | Boyd | 604/180 X |
| 4,057,066 | 11/1977 | Taylor | 604/180 |

Primary Examiner—Dalton L. Truluck
Attorney, Agent, or Firm—Townsend & Townsend

[57] ABSTRACT

A catheter restraint comprises an adhesive backing which is applied to the patient's skin at a location adjacent the catheter entry point. At least three adhesive strips emanate from the non-adhesive surface of the backing along a straight line allow attachment of both the catheter and catheter tubing to the backing. At least one additional adhesive strip is provided spaced-apart from the line so that the catheter tubing may be looped backward and secured to the backing to help prevent the catheter from being dislodged by pulling on the catheter tubing. The catheter restraint allows the catheter to remain in place while the catheter tubing is changed.

4 Claims, 4 Drawing Figures

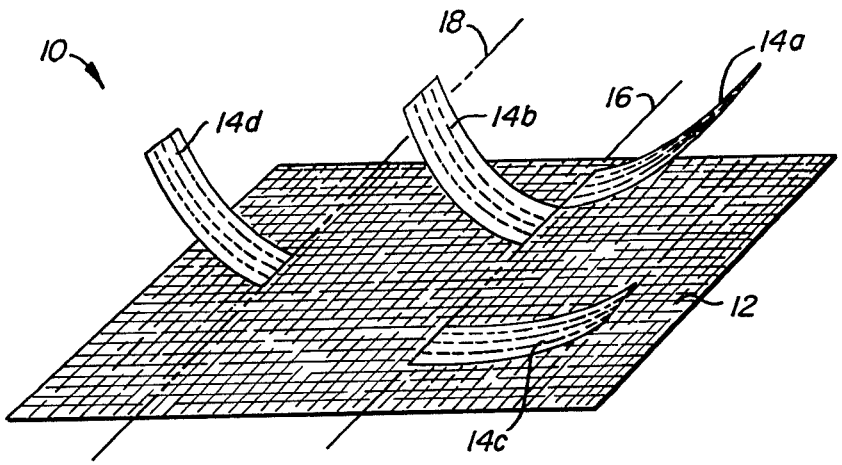
FIG._1.
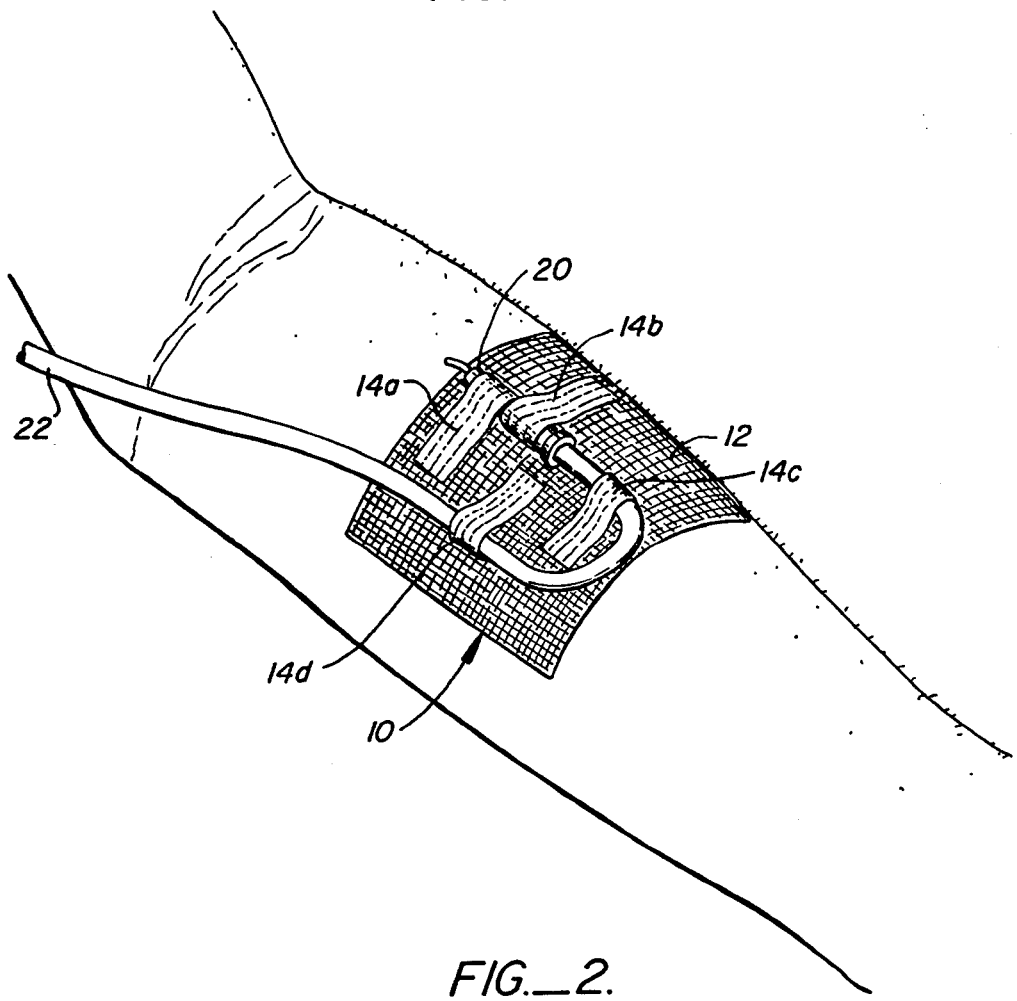
FIG._2.

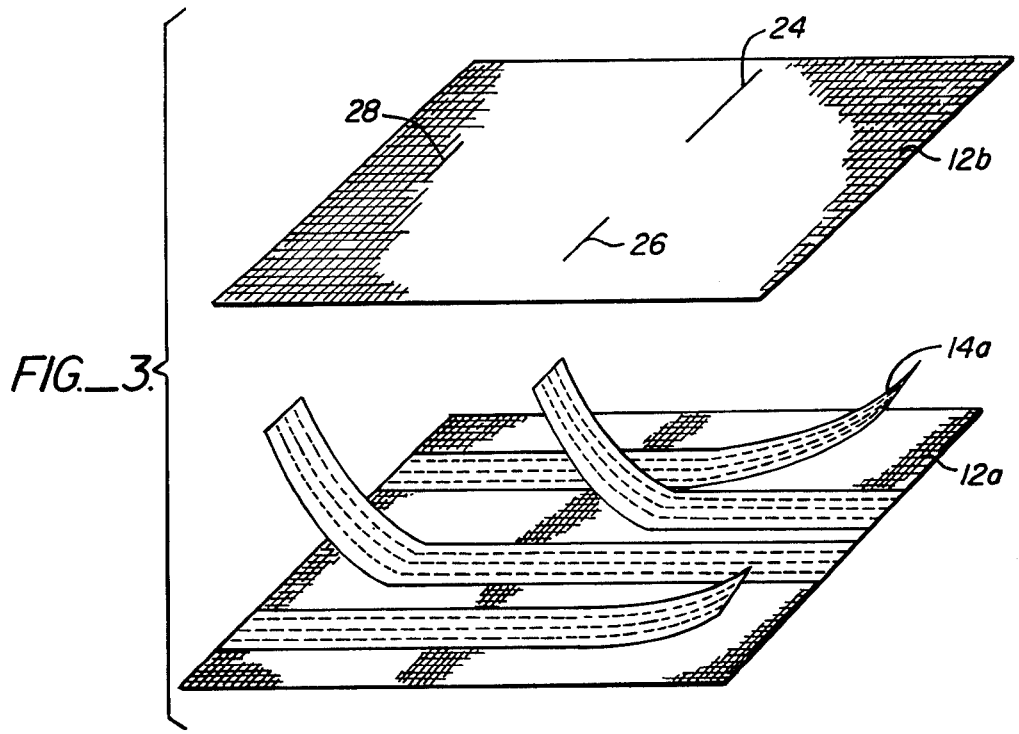
FIG._3.
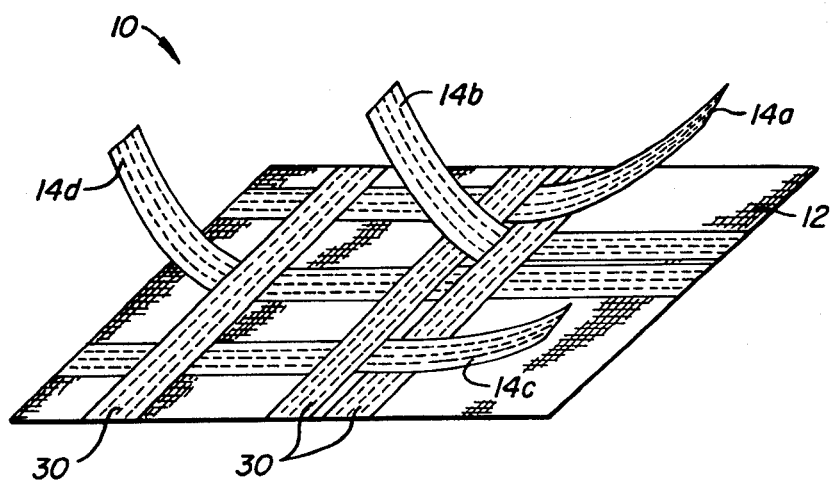
FIG._4.

INTRAVENOUS CATHETER RESTRAINT

BACKGROUND OF THE INVENTION

1. Field of the Invention

The present invention relates generally to devices for securing a catheter and catheter connecting tube to a patient undergoing treatment.

A catheter is a slender, flexible tube of metal, rubber or plastic which is inserted through a patient's skin to distend or maintain an opening into an internal body cavity. Most catheters are used for intravenous administration of drugs, nutrients and the like, where the catheter is connected to a supply bottle by a flexible connecting tube. The catheter includes a female receptacle at one end for receiving the catheter connecting tube (referred to hereinafter as the "catheter tubing" or "catheter connecting tubing"). The catheter is inserted beneath the patient's skin, leaving the receptacle located adjacent the point of insertion and must somehow be secured to prevent the catheter from being accidentally dislodged by pulling on the catheter connecting tube.

2. Description of the Prior Art

Heretofore, the most common method for attaching a catheter to a patient has been by using a strip of adhesive tape placed directly on the patient's skin and over the catheter receptacle. The connecting tubing could then be inserted into the receptacle and, typically, the tubing would also be taped at one or more locations to the patient. It has been found, however, that the use of one or two strips of adhesive tapes is usually insufficient to hold the catheter in place. Perspiration often causes moisture to loosen the tape, requiring the addition of more and more strips of tape to hold the catheter in place. This is particularly a problem since the catheter tubing must be replaced every twenty-four hours as a matter of law in most states. The constant removal and replacement of adhesive tape can be very irritating and uncomfortable for the patient.

A number of devices have been proposed to overcome the deficiencies of using adhesive tape. U.S. Pat. No. 2,727,512 to Muller discloses an adhesive tape strip having a sponge rubber pad which bears directly against the catheter and/or catheter connecting tubing. Since the sponge rubber pad does not adhere to the patient's skin, however, the catheter and catheter tubing are free to move about thereunder. It is desirable to provide a catheter restraint which does not allow such movement.

U.S. Pat. No. 3,677,250 to Thomas discloses a catheter tubing restraint comprising an adhesive tape backing having integral strips formed from the same sheet of which the backing is formed. The restraint is intended for anchoring catheter tubing remote from the entrance site of the catheter itself. Such a catheter restraint allows the catheter tubing to be secured and removed from the straps without having to remove the backing from the patient's skin. This is an improvement over the use of conventional adhesive tape, however, the straps emanate from the edges of the adhesive pad and any force tending to dislodge the catheter tubing would also tend to peel the adhesive backing from the patient's skin. This is undesirable since over time the backing can work its way loose. It is desirable to provide a catheter restraint having a reduced tendancy to be peeled from the skin when a pulling force is applied to the catheter connecting tubing.

Other devices suitable for use as a catheter restraint are disclosed in U.S. Pat. No. 3,046,989 to Hill and U.S. Pat. No. 4,074,397 to Rosin.

SUMMARY OF THE INVENTION

The present invention is a catheter restraint comprising a flexible, adhesive backing and a plurality of flexible, adhesive strips emanating from the non-adhesive surface of the backing. At least three of the adhesive strips are located along a substantially straight line, with at least two strips located adjacent each other and near one edge of the backing. At least one additional adhesive strip emanates from the non-adhesive surface of the backing along a second line which is usually parallel to, but spaced apart from the first line. In this way, the pair of strips adjacent one edge of the backing can be used to secure a catheter receptacle to the backing, while the remaining strips are used to form a loop in the catheter tubing which helps assure that the catheter will not be dislodged.

BRIEF DESCRIPTION OF THE DRAWINGS

FIG. 1 illustrates the preferred embodiment of the catheter restraint of the present invention.

FIG. 2 illustrates the catheter restraint of FIG. 1 placed on a patient's arm and used to secure a catheter and associated catheter connecting tubing.

FIG. 3 illustrates a first construction for the catheter restraint.

FIG. 4 illustrates an alternate construction for the catheter restraint.

DESCRIPTION OF THE PREFERRED EMBODIMENT

Referring to FIGS. 1 and 2, a catheter restraint 10 comprises a patch or backing 12 having a pressure-sensitive adhesive on one surface thereof for binding to a patient's skin. The backing 12 is formed from a thin, flexible material, usually a woven fabric, although other paper and polymeric materials would also be suitable. The backing 12 may comprise one or more layers and the various layers need not comprise the same material. Depending on the material, it may be desirable to strengthen the material with high tensile strength fibers or cords which run through the material in either a parallel or crossing pattern.

A plurality of adhesive strips 14 emanate from or through the non-adhesive side of the backing 12 and may be attached thereto by pressure. As illustrated in FIGS. 1 and 2, the underside of the backing 12 is the adhesive surface, while the upper surface is the non-adhesive surface having the strips 14 secured thereto. At least three of the strips 14 will be located along a first line 16, with at least two of the strips located adjacent one another at one edge of the backing 12. At least one additional strip 14 will be located along a second line 18 which is spaced apart from but generally parallel to the first line 16. The second line 18 may, in fact, intersect line 16 and it is necessary only that the line be located so that the catheter connecting tubing may be formed into a loop when secured by the restraint 10.

In the preferred embodiment, three strips 14a, 14b and 14c are located along the first line 16, with strips 14a and 14b located near one edge and third strip 14c located substantially toward the opposite edge of the backing 12. A single additional strip 14d is located along the second line 18. Additional strips may be added along either or both lines 16 and 18, although they will usually not be necessary.

The dimensions of the components of the catheter restraint 10 are not critical. The backing 12 will usually be rectangular, having minimum dimensions chosen to assure adequate adherance to the patient's skin. A width of about 3 cm and a length of about 5 cm will usually be adequate, although larger dimensions may be used to provide even better adherence. The shape of the backing 12, of course, can vary widely so long as a sufficiently large base is provided for securing the adhesive strips thereto.

The adhesive strips 14 are usually elongate rectangles having sufficient length to provide adequate adherence to the non-adhesive side of the backing 12. Additionally, it is desirable that the strips 14a and 14b be sufficiently narrow so that they can be folded over a catheter receptacle 20, as illustrated in FIG. 2. Strips usually have a width of about ½ cm and a length of about 2 cm.

With the exception of strips 14a and 14b, it is desirable that the strips be placed inward from the edges of the backing 12 so that any stress exerted on the intravenous tubing does not tend to peel off an edge of the backing 12. Pulling on the central portion of the backing 12 is less likely to pull the backing from the skin than peeling from an edge. The strip 14a, of course, must be located substantially adjacent one edge of the backing 12 so that it can secure catheter the receptacle 20 near the point of insertion (FIG. 2). Generally, the lines 16 and 18 will be spaced inwards approximately ⅓ of the distance from each edge of the backing 12.

Referring now in particular to FIG. 2, the catheter restraint 10 is secured to a patient's skin by placing the adhesive surface downward onto the skin. The restraint 10 will be located so that the strip 14a is adjacent the location where the catheter 20 has been inserted or is to be inserted. After both the catheter 20 and the restraint 10 are in place, the catheter receptacle 20 is placed down on the backing 12 along the line 16 and between the strips 14a and 14b. The strips 14a and 14b are then folded in opposite directions so that their adhesive surfaces cover both the receptacle and a portion of the non-adhesive surface of the backing 12. In this way, force exerted against the catheter receptacle in either direction is prevented from dislodging the receptacle. Moreover, the particular "criss-cross" pattern of the strips 14a and 14b largely prevents the catheter receptacle from being rotated, which might dislodge the catheter from the patient.

After securing the catheter receptacle 20, catheter tubing 22 is inserted into the receptacle. The tubing is then formed into a loop, first by following outward along line 16 and then folding back to travel in the opposite direction along line 18. Strips 14c and 14d are then used to fix the tubing 22 into the loop and the tubing may then be connected to the desired fluid or discharge bottle. Moreover, the catheter connecting tubing 22 may be changed without disturbing the catheter 20 by simply peeling strips 14c and 14b to allow removal of the tubing. Such a change is not irritating to the patient since the strips adhere to the backing 12, not to the patient's skin.

Referring now to FIG. 3, the catheter restraint 10 can be formed as a two-layer structure having a lower layer 12a and an upper layer 12b. The adhesive strips 14 are sandwiched between the two layers and extend upward through slots 24, 26 and 28. The lower surface of layer 12a includes the pressure-sensitive adhesive. The layers 12a and 12b can be sealed to each other by a variety of means. Usually, a water insoluble glue will be used to seal the layers.

An alternate method of construction of the catheter restraint 10 is illustrated in FIG. 4. The adhesive strips 14 are secured directly to the upper surface of a single-layer backing 12. The strips 14 will usually be secured by a heat-activated permanent adhesive, although other means of permanently securing them to the backing 12 will be adequate. To assure that the strips 14 are not peeled from the backing, a crossing pattern of flexible strips 30 is provided, which strips intersect the strips 14 at the appropriate locations to define the lines 16 and 18. The strips 30 are, of course, permanently secured to the backing 12 to assure that the strips 14 will not be dislodged.

The catheter restraint 10 is useful for securing the catheter itself proximate the catheter entrance site on the patient's skin, as illustrated in FIG. 2. Additionally, the end of the catheter connecting tube 22 which plugs into the catheter receptacle 20 may be separately secured to the restraint 10 using additional adhesive strips 14c and 14d.

Although the present invention has been described in detail by way of illustration and example for purposes of clarity of understanding, it will be obvious that certain changes and modifications may be practiced within the scope of the appended claims.

What is claimed is:

1. A catheter restraint for securing a catheter and catheter connecting tubing to a patient's skin, said restraint consisting of:
    a flexible backing having a pressure-sensitive adhesive on one surface thereof for securing to the patient's skin, the opposite surface of the backing being non-adhesive;
    at least three elongate, flexible strips, each having a pressure-sensitive adhesive on one surface thereof and being attached at one end to the non-adhesive surface of the flexible backing in a straight line with at least two of said strips being located adjacent each other along said line and having their adhesive surfaces facing in opposite directions so that the said two strips are capable of wrapping around the catheter and adhering to the non-adhesive surface of the backing on opposite sides of the catheter; and
    at least one additional, elongate, flexible strip located along a second line spaced apart from the first so that a loop may be formed in the catheter tubing which is secured to the backing.

2. A catheter restraint as in claim 1, wherein the flexible backing is generally rectangular, having dimensions of at least 3 cm by 5 cm and wherein said first and second lines are spaced apart in the direction of the 5 cm dimension.

3. A catheter restraint as in claim 1, wherein said two adjacent strips are located substantially at one edge of the backing.

4. A catheter restraint as in claim 2, wherein said first and second lines are located approximately one-third of the way in from opposite edges of the rectangle.

* * * * *